US00PP11461P

United States Patent [19]

Westhoff

[11] Patent Number: Plant 11,461

[45] Date of Patent: Jul. 25, 2000

[54] PETUNIA PLANT NAMED 'WESKLEIPUR'

[75] Inventor: Heinrich Westhoff, Südlohn-Oeding, Germany

[73] Assignee: Josef & Heinrich Westhoff Gartenbau-Spezialkulturen, Sudlohn-Oeding, Germany

[21] Appl. No.: 09/165,392

[22] Filed: Oct. 2, 1998

[51] Int. Cl.[7] ..... A01H 5/00

[52] U.S. Cl. ..... Plt./356

[58] Field of Search ..... Plt./356

[56] References Cited

U.S. PATENT DOCUMENTS

P.P. 10,086 10/1997 Rother ..... Plt./356
P.P. 10,426 6/1998 Danziger ..... Plt./356

*Primary Examiner*—Howard J. Locker
*Assistant Examiner*—Wendy A Baker

[57] ABSTRACT

A distinct cultivar of Petunia plant named 'Weskleipur', characterized by its numerous bright purple flowers; cascading and freely branching growth habit; relatively small dark green leaves; and good weather tolerance.

2 Drawing Sheets

BACKGROUND OF THE INVENTION

The present invention relates to a new and distinct cultivar of Petunia plant, botanically known as *Petunia axillaris,* and hereinafter referred to by the cultivar name Weskleipur.

The new Petunia is a product of a planned breeding program conducted by the Inventor in Südlohn-Oeding, Germany. The new Petunia originated from a cross made by the Inventor in 1996 in Südlohn-Oeding, Germany, of a seedling selection of *Petunia axillaris* identified as Sylvana purple as the female, or seed, parent with a seedling selection of *Petunia axillaris* identified as Sylvana 95/306 as the male, or pollen, parent.

Asexual reproduction of the new cultivar by terminal cuttings taken at Südlohn-Oeding, Germany, has shown that the unique features of this new Petunia are stable and reproduced true to type in successive generations.

SUMMARY OF THE INVENTION

Plants of the cultivar Weskleipur have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Weskleipur'. These characteristics in combination distinguish 'Weskleipur' as a new and distinct cultivar:

1. Numerous bright purple flowers.

2. Cascading and freely branching growth habit.

3. Relatively small dark green leaves.

4. Good weather tolerance, particularly tolerant to rain and wind.

Plants of the cultivar Weskleipur are similar in flower color to plants of the cultivar Revolution Purplepink, disclosed in U.S. Plant Pat. No. 6,915. However in side-by-side comparisons conducted in Südlohn-Oeding, Germany, plants of the cultivar Weskleipur differ from plants of the cultivar Revolution Purplepink in the following characteristics:

1. Leaves of plants of the new Petunia are smaller and darker green than leaves of plants of the cultivar Revolution Purplepink.

2. Plants of the new Petunia have smaller but more numerous flowers than plants of the cultivar Revolution Purplepink.

3. Plants of the new Petunia flower earlier than plants of the cultivar Revolution Purplepink.

4. Plants of the new Petunia exhibit better weather tolerance, particularly to rain and wind, than plants of the cultivar Revolution Purplepink.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a plants of the new Petunia planted in a window box.

The photograph on the second sheet comprises a close-up view of typical flowers and leaves of the new Petunia. Flower and foliage colors in the photographs may appear different than the actual colors due to light reflectance.

DETAILED BOTANICAL DESCRIPTION

In the following description, color references are made to The Royal Horticultural Society Colour Chart except where general terms of ordinary dictionary significance are used. Twelve-week old plants grown in 12.5-cm containers used for the description were grown under greenhouse conditions which closely approximate commercial production conditions during the summer in West Chicago, Ill.

Botanical classification: *Petunia axillaris* cultivar Weskleipur.

Parentage:

*Female parent.*—*Petunia axillaris* seedling selection identified as Sylvana purple, not patented.

*Male parent.*—*Petunia axillaris* seedling selection identified as Sylvana 95/306, not patented.

Propagation:

*Type cutting.*—Terminal vegetative cuttings.

*Time to initiate and develop roots.*—About 14 days at 20° C. soil temperature.

*Rooting habit.*—Numerous, fine, fibrous, and well-branched.

Plant description:

*Form*.—Indeterminate, decumbent, cascading, viscid, glandular pubescent.

*Branching habit*.—Freely branching, lateral branches typically form at every node. Plants typically do not require pinching.

*Plant height* (*from soil level to top of plant plane*).—About 6 cm.

*Spreading area of plant*.—About 49 cm, cascading, decumbent.

*Vigor*.—Moderate to vigorous.

*Foliage description*.—Leaves simple, generally symmetrical and long persisting. Leaves usually alternate, somewhat fleshy, glandular. Length: About 5 cm. Width: About 3.6 cm. Thickness: About 1 mm. Aspect: Typically horizontal. Shape: Ovate. Apex: Acute. Base: Cuneate. Margin: Entire. Texture: Upper surface: Smooth. Lower surface: Midvein and lateral veins, pubescent. Margin: Pubescent. Color: Young foliage, upper surface: 147A. Young foliage, lower surface: Close to 147B. Mature foliage, upper surface: 147A. Mature foliage, lower surface: 147B. Peduncle: Length: About 1 cm. Diameter: About 2.5 mm. Texture: Pubescent. Color: 146B.

*Stem description*.—Diameter: About 3 mm. Internode length: About 2.5 cm. Texture: Very pubescent, glandular. Color: Green, 146A.

Flower description:

*Flower type and habit*.—Large, single, salverform flowers, facing upward and outward, axillary. Calyx five-parted, petals united into a flower tube. Flowers typically last 7 to 14 days, dependent on weather conditions. Flowers non-persistent.

*Natural flowering season*.—Long day responsive, continuously flowers from spring through fall.

*Fragrance*.—None detected.

*Quantity*.—Very freely flowering with numerous flowers per plant.

*Corolla*.—Diameter: About 4.4 cm. Height: About 3.5 cm. Flower tube width at distal end: About 1.2 cm. Petal quantity: Five, fused. Petal apex: Acute to acuminate. Margin: Entire. Texture: Pubescent on lower surface, smooth and satiny on upper surface; iridescent. Color: Flower throat (inside): 83A. Flower tube color (outside): 82C/82D. Petal color, upper surface: 74A/74B. Petal vein color, upper surface: 83A/83B. Petal color, lower surface: 81A to 81C.

*Sepals*.—Quantity: Five. Length: About 1.4 cm. Width: About 2.5 mm. Shape: Linear. Apex: Acute. Margin: Entire. Aspect: Upright. Texture: Pubescent. Color: 144A.

*Peduncle*.—Strength: Wiry, flexible. Length: About 2.7 cm. Width: Narrow, about 1 mm. Texture: Pubescent. Color: 144A.

*Reproductive organs*.—Stamens: Stamen number: Five. Anther color, before dehiscence: 93D. Filament color: Greenish white. Pollen color: 96B. Pistils: Stigma color: Green. Style color: Greenish white.

Weather tolerance: Good tolerance to rain and wind has been observed.

Disease resistance: Resistance to diseases common to Petunia has not been observed.

Seed production: Seed production has not been observed.

It is claimed:

1. A new and distinct cultivar of Petunia plant named 'Weskleipur', as illustrated and described.

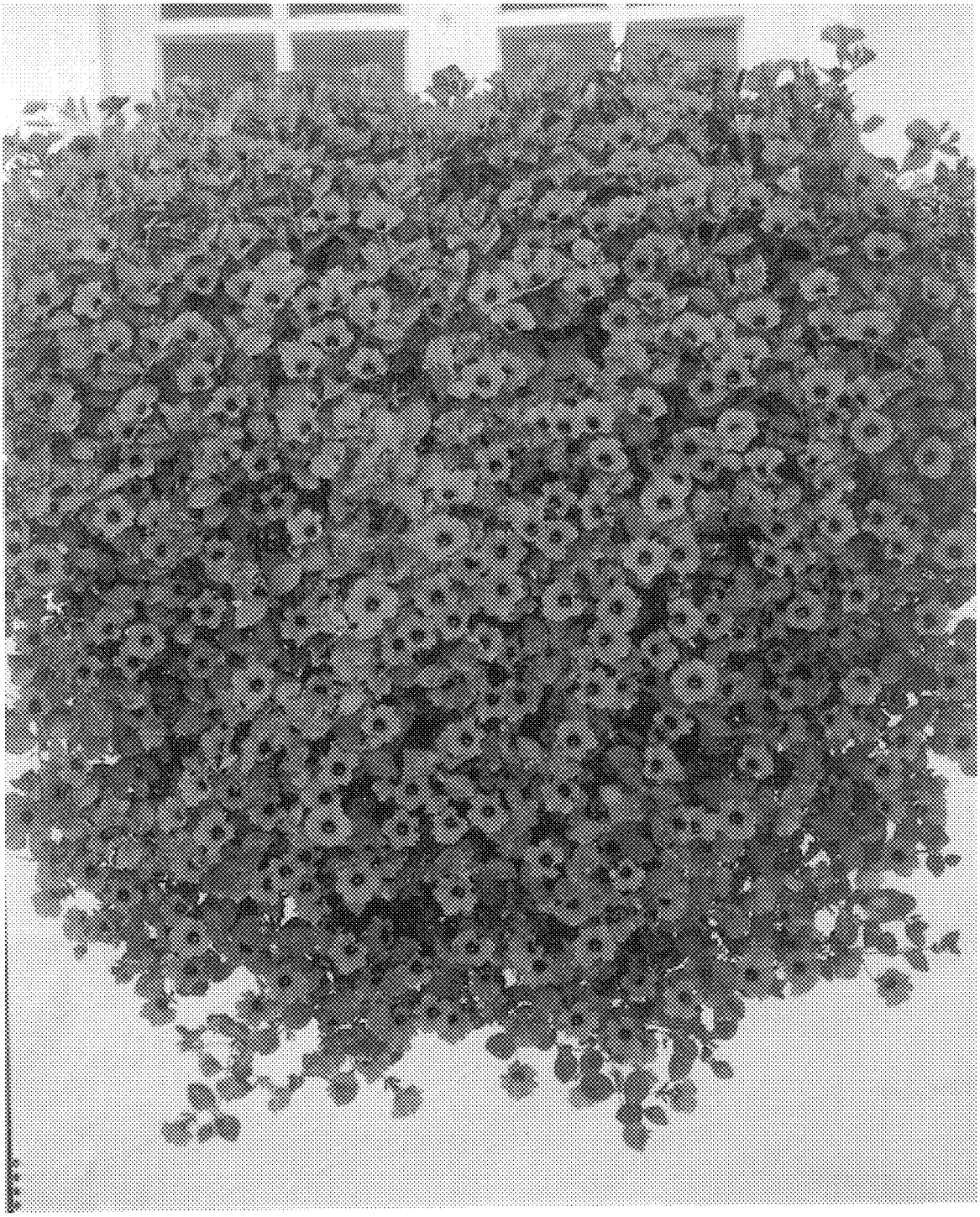

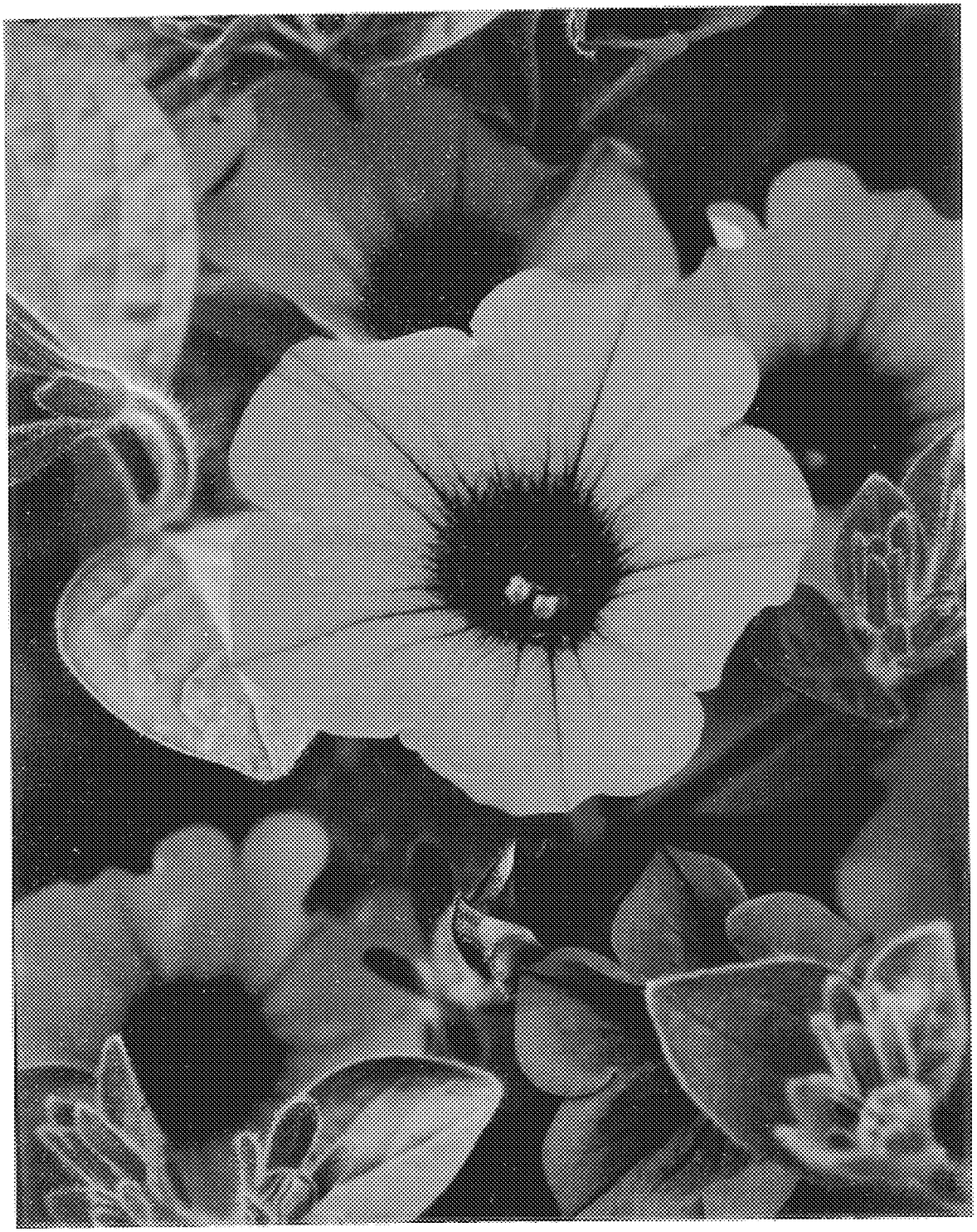

* * * * *